United States Patent [19]

Hruby et al.

[11] 4,430,326

[45] Feb. 7, 1984

[54] METHOD OF DIMINISHING GLUCOSE LEVELS RESULTING FROM ENDOGENOUS GLUCAGON

[75] Inventors: Victor J. Hruby; Marvin D. Bregman, both of Tucson, Ariz.

[73] Assignee: University Patents, Inc., Norwalk, Conn.

[21] Appl. No.: 333,376

[22] Filed: Dec. 22, 1981

[51] Int. Cl.³ .............................................. A61K 37/02
[52] U.S. Cl. .................................................. 424/177
[58] Field of Search ....................................... 424/177

[56] References Cited

U.S. PATENT DOCUMENTS

| 3,715,348 | 2/1973 | Smith | 424/177 |
| 4,206,199 | 1/1980 | Fujino et al. | 424/177 |
| 4,221,777 | 9/1980 | Nishino | 424/177 |

OTHER PUBLICATIONS

Bergman et al., *The Journal of Biological Chemistry*, 255, pp. 11725-11731 (1980).
Lin et al., *Biochemistry*, 14, pp. 1559-1563 (1975).
Epand et al., *Biochemica et Biophysica Acta*, 393, pp. 236-246 (1975).
Wright et al., *The Journal of Biological Chemistry*, 253, pp. 6338-6340 (1978).

*Primary Examiner*—Delbert R. Phillips
*Assistant Examiner*—F. T. Moezie
*Attorney, Agent, or Firm*—Merriam, Marshall & Bicknell

[57] ABSTRACT

Effects of endogenous glucagon in mammals are diminished by administration of compositions including certain semi-synthetic analogs of glucagon. Preferred analogs include [$N^{\alpha}$-TNB, HArg$^{12}$]glucagon and [dHis$^{1}$]-[$N^{\alpha}$-TNB, HArg$^{12}$]glucagon, parenterally administered at doses of from about 0.05 to about 50 mg of analog per kg of body weight.

15 Claims, 3 Drawing Figures

METHOD OF DIMINISHING GLUCOSE LEVELS RESULTING FROM ENDOGENOUS GLUCAGON

BACKGROUND

The invention made herein was supported in part by funding from the National Institutes of Health, Department of Health and Human Services.

The present invention relates generally to methods for diminishing the glucose levels resulting from endogenous glucagon in mammals and more particularly to administration of glucagon analogs which antagonize the effects of endogenous glucagon in mammals.

Glucagon is a 29 amino acid peptide hormone which is secreted by cells in the islets of Langerhans of the mammalian liver. By convention, the amino acid residues of this peptide hormone are numbered sequentially from the amino terminal carbon atom through the carboxyl terminal carbon atom as follows:

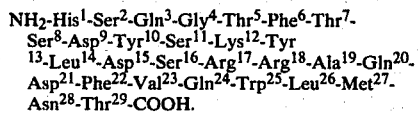

In the above formula the following abbreviations are used: His=histidine; Ser Gln=glutamine; Gly=glycine; Thr=threonine; Phe=phenylalanine; Asp=aspartic acid; Tyr=tyrosine; Lys=lysine; Leu=leucine; Arg=arginine; Ala=alanine; Val=valine; Trp=tryptophan; Met=methionine; Asn=asparagine.

Also by convention, the amino groups of the various amino acids are assigned nomenclature corresponding to that given to the carbon atom to which the amino group is covalently bonded in the amino acid. The carbon atom adjacent to the carboxylic group is the alpha ($\alpha$) carbon atom, the second carbon atom from the carboxyl group is beta ($\beta$), the third gamma ($\delta$), the fourth delta ($\delta$), the fifth epsilon ($\epsilon$), and so forth, so that the N-terminal amino group attached directly to the $\alpha$carbon atom of the N-terminal amino acid is called the $N^\alpha$ amino group and the amino group attached to the last carbon atom of the Lysine-12 residue (i.e., —CH$_2$—CH$_2$—CH$_2$—CH$_2$—NH$_2$) is the $N^\epsilon$ amino group.

Endogenous glucagon has numerous direct and indirect effects on glucose levels in vivo. It directly raises the blood sugar (glucose) level in mammals by promoting the breakdown of glycogen (glycogenolysis), the storage form of glucose in the mammalian liver. See, White, et al., *Principles of Biochemistry*, pp. 478–479, 1101–1102 (5th ed., 1973).

Conversion of glycogen to glucose is brought about through stimulation of the liver membrane adenylate cyclase system of mammals. (See White, supra, pp. 1102–03). The hormone also maintains or increases the mammalian circulating glucose levels by reducing the rate of glycogen synthesis, promoting the breakdown of protein and promoting the use of fat as an energy source. See, White, supra, pp. 1102–03).

Considerable evidence exists which indicates that glucagon is involved in the pathogenesis of diabetes mellitus. The central role of a relative or absolute deficiency of insulin in the development of diabetes has been recognized since the experiments of von Merring and Minnowski in 1889, [See, von Merring et al., *Arch. Exp. Path. Pharmak.*, 26, p. 371 (1889)], and the identification of insulin in 1922. See, Banting, et al., *J. Lab. Clin. Med.*, 7, p. 251 (1922). The development, in the late 1960's, of radioimmunoassay techniques for measuring glucagon revealed a relative or absolute excess of circulating glucagon in virtually all forms of human and animal diabetes See, Unger, et al., *Lancet, i*, p. 14 (1975); and Unger, et al., *Metabolism*, 27, p. 1691 (1978). These observations led to the 'bihormonal' concept of diabetes as a disorder due to a relative lack of endogenous insulin effect and a relative excess of endogenous glucagon effect. See, Unger, et al., *Lancet*, supra, and Unger, et al., *Metabolism*, supra.

The discovery that somatostatin suppresses both insulin and glucose secretion provided additional evidence of the importance of glucagon in glucose homeostasis. See, Mortimer, et al., *Lancet, i*, p. 697 (1974); and Koerker, *Science*, 184, p. 482 (1974). When secretion of glucagon and insulin was suppressed by infusion of somatostatin, there was a fall in blood glucose concentration. See, Koerker, et al., supra. However, concomitant infusion of glucagon reversed the fall in the blood glucose level. See, Sakuari, et al., *J. Clin. Invest.*, 54, p. 1395 (1974); and Alford, et al., *Lancet, ii*, p. 974 (1974). Furthermore, infusion of somatostatin to inhibit secretion of endogenous glucagon reduced the high blood sugar levels (hyperglycemia) of diabetic human patients. See, Gerich, et al., *J. Med.*, 291, p. 544 (1974); and Gerich, et al., *N. Eng. J. Med.*, 292, p. 985 (1975).

The recognition that excessive glucagon secretion is a contributing factor in the metabolic abnormalities of diabetes has prompted substantial research into development of methods and materials for antagonising the effects of endogenous glucagon on target tissues. See, Bregman, et al., *FEBS Letters*, 101, p. 191 (1979); and Cote, et al., *Biochim. Biophys. Acta*, 582, p. 295 (1979).

Using the naturally-occurring peptide hormone as a starting point, some researchers have attempted to develop antagonistic glucagon analogs via semi-synthetic methods, i.e., creation of glucagon analogs either by chemical modification of the reactive side groups of the endogenous hormone's amino acid residues [see, Hruby, et al., *Metabolism*, 25, pp. 1323–1324 (1976); and Epand, et al., *Biochim. Biophys. Acta*, 393, p. 236 (1975)], or by removal of one or more of the amino acid residues from either the $N^\alpha$ terminal or carboxyl terminal regions of the native peptide hormone. [See, Wright, et al., *J. Bio. Chem.*, 253, pp. 6338–6340 (1978); Lin, et al., *Biochemistry*, 14, pp. 1559–1563 (1975); and Rodbell, et al., *Proc. Nat. Acad. Sci., USA*, 68, pp. 909–931 (1971)].

Of interest to the background of the present invention are early studies which indicated that the endogenous hormone's carboxyl terminal region (amino acid residues 22–29) was not essential to the hormone's binding to the adenylate cyclase activator receptors or for stimulation of adenylate cyclase activity. See, Wright, et al., supra, p. 6640. It has also been reported that removal of the histidine-1 residue results in an analog which acts as a weak partial activator (agonist) on the adenylate cyclase system. See, Lin, et al., supra, p. 1563.

It was also reported that the introduction of hydrophilic groups such as trifluoroacetyl [See, Lande et al., *Endocrinology*, 90, pp. 597–604 (1972)], acetyl [See, Desbuquois, *Eur. J. Biochem.*, 60, pp. 335–347 (1975)] and carbamoyl [See, Epand, et al., supra, pp. 132–136 (1975)]produced weak activators (agonists) of the adenylate cyclase system relative to native glucagon. Addition of the hydrophilic guanidyl group to the other free amino group of glucagon, the $N^\epsilon$ amino group of the lysine-12 residue (i.e., [12-homoargine]glucagon) produced an analog which was reported to be a full agonist. See, Bregman, et al., *J. Biol. Chem.*, 255, pp. 11725–11731 (1980).

Of particular interest to the background of the present invention are the reports that the addition of a hydrophobic (lipophilic) substituent to the $N^{60}$ or $N^\epsilon$ amino groups and hydrophobic or hydrophilic substituents to the unaltered amino group (if any) produced analogs which stimulated adenylate cyclase activity. See, Epand, et al., *Biochim. Biophys. Acta*, 393, pp. 242–243 (1975). Semi-synthetic analogs reported to act as agonists included: $N^\alpha$-trinitrophenyl glucagon, $N^\alpha,N^\epsilon$-di(trinitrophenyl)-glucagon, $N^\alpha$-trinitrophenylguanidyl glucagon (=[$N^\alpha$-TNB,HArg$^{12}$]glucagon); $N^\epsilon$-trinitrophenyl carbamyl glucagon (=[$N^\epsilon$-carbamoyl,$N^\epsilon$-TNB]glucagon). See, Epand, supra. Although a later study reported that lipophilic substitution at the $N^\alpha$ position alone (i.e., $N^\alpha$-trinitrophenyl glucagon) resulted in an antagonist relative to glucagon stimulated adenylate cyclase activity, the same study also classified the analog as a partial agonist toward glycogenolytic stimulation. See, Cote, et al., supra. Also of interest to the background of the present invention was the report of a semi-synthetic analog of glucagon which exhibited antagonist behaviour toward glucagon stimulated adenylate cyclase activity. See, Bregman, et al., *FEBS Letters*, 101, pp. 191–193 (1979). The glucagon antagonist examined there (des-histidine-1) ($N^\epsilon$-phenylthiocarbamoyl)-glucagon ([dHis$^1$][$N^\epsilon$-PTC]glucagon), was synthesized through addition of the hydrophobic PTC moiety to the $N^\epsilon$ amino group and deletion of the $N^\alpha$ amino acid residue. Although exhibiting antagonistic characteristics, the [dHis$^1$][$N^\epsilon$-PTC]glucagon analog was reported to be a relatively weak inhibitor, having only 1/18 the affinity of endogenous glucagon for the adenylate cyclase receptor site.

There continues to exist, therefore, a long-standing need in the art for a method of antagonizing the effects of endogenous glucagon in mammals.

Specifically incorporated by reference herein for the purpose of illustrating the background of the invention and the prior art is the publication by the inventors and their co-worker appearing in *J. Biol. Chem.*, 255, pp. 11725–11731 (Dec. 25, 1980).

BRIEF SUMMARY

The present invention provides a novel method for diminishing the glucose levels resulting from endogenous glucagon in mammals which comprises parenterally administering antagonistically effective amounts of a glucagon analog having a positive charge neutralizing, lipophilic and/or steric-hindering substituent on the $N^\epsilon$ amino group and either (1) a positive charge neutralizing, lipophilic and/or steric-hindering substituent on the $N^\alpha$ amino group of histidine, or (2) the $N^\alpha$ amino group of histidine deleted with the addition of a positive charge neutralizing, lipophilic and/or steric-hindering substituent, or (3) the $N^\alpha$-histidine amino acid deleted with the addition of a positive charge neutralizing, lipophilic and/or steric-hindering substituent to the amino group of serine-2.

Presently preferred compounds include the semisynthetic analogs of glucagon, [$N^\alpha$-TNB, HArg$^{12}$]glucagon, and [dHis$^1$][$N^\alpha$-TNB, HArg$^{12}$]glucagon.

Pharmaceutical compositions of the invention comprise effective amounts of the analogs in combination with a pharmaceutically acceptable diluent, adjuvant or carrier. Effective doses may range from about 0.05 to about 50 mg of analog per kg of mammalian body weight and preferably about 0.1 to about 10 mg/kg.

Practice of the methods of the invention produces a dramatic initial decrease in blood glucose levels in vivo upon a single injection into hyperglycemic mammals. Continuous infusion causes an even more dramatic and sustained decrease in the blood glucose level of diabetic mammals, and this effect persists for some time after the infusion is stopped.

Other aspects and advantages of the invention will become apparent upon consideration of the following detailed description wherein FIGS. 1 through 3 graphically illustrate the glucagon antagonistic effect of the preferred methods of the invention.

DETAILED DESCRIPTION

Figure 1:
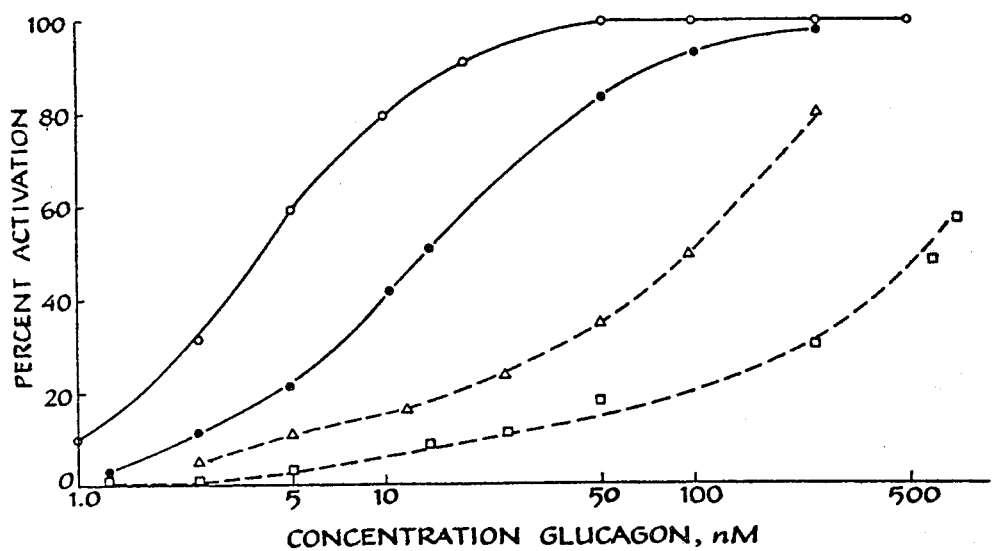

The following examples illustrate practice of the invention according to certain preferred procedures. More specifically, they treat: preparation of exemplary glucagon antagonist compounds, [1-$N^\alpha$-trinitrobenzene, 12-homoarginine]glucagon and [1-des-histidine][2-$N^\alpha$-trinitrobenzene, 12-homoarginine]glucagon, by semi-synthetic methods; and use of the compound to diminish glucose levels resulting from glucagon in vitro and in vivo.

EXAMPLE 1

Preparation of [$N^\alpha$-TNB, HArg$^{12}$]Glucagon

1. Materials

Crystalline glucagon obtained from Elanco Co. was purified on DEAE A-25 Sephadex to remove desamidoglucagon. DEAE Sephadex A-25, SP-Sephadex C-25 and Sephadex G-10 were purchased from Pharmacia. Trinitrobenzenesulfonic acid was obtained from Pierce. O-Methylisourea hydrogen sulfate was obtained from Aldrich. Carboxypeptidase A, chymotrypsin and phosphokinase were purchased from Sigma, and aminopeptidase M from Rohm and Haas. [$\alpha$-$^{32}$P]-ATP and cyclic [$^3$H]AMP were obtained from New England Nuclear. All other chemicals were of reagent grade.

2. Synthesis

O-Methylisourea-H$_2$SO$_4$ (3.4 g) was dissolved in 20 ml of H$_2$O. Ba(OH)$_2$ (6 g) was added slowly to the stirring solution. The mixture was filtered through two sheets of Whatman #1 filter paper on a Buchner funnel. The supernatant was centrifuged for 15 min at 3000 times g. The clear supernatant was carefully removed from the BaSO$_4$ pellet and adjusted to pH 11.0. Glucagon (200 mg) was added to 10 ml of water and the solution adjusted to pH 11.0. The two solutions were cooled to 4° C. and then combined. The reactions were terminated after 8 h by adding glacial acetic acid (20 ml). The product [HArg$^{12}$]glucagon was desalted on a G-10 Sephadex column (2.5×75 cm) developed with 30% acetic acid.

A trinitrophenyl group was introduced at the $N^\alpha$ position of [HArg$^{12}$]glucagon as described in Epand, et al., *Biochim. Biophys. Acta*, 576, 372–384 (1975). Verification of incorporation of the TNB group was done through use of molar extinction coefficients at 350 nm where only TNB absorbs. The product here was the equivalent of a mono-substituted product. Aminopeptidase digestion of [$N^\alpha$-TNB, HArg$^{12}$]glucagon did not release any histidine or serine, while similar treatment of [HArg$^{12}$]-glucagon and [dHis][HArg$^{12}$]glucagon did. Acid hydrolysis of [$N^\alpha$-TNB, HArg$^{12}$]glucagon resulted in significant regeneration of the free amino acid from the TNB-modified histidine-1 amino acid.

3. Purification and Analysis

Ultraviolet-visible measurements were made on a Gilford 240 spectrophotometer. Several hormone derivatives were purified on a DEAE-Sephadex A-25 column (1.2×15 cm). They were solubilized in 7 M urea and the column developed at 5° C. with 70 ml of 0.01 M Tris (pH 7.7) followed by 60 ml of 0.5 M NaCl in 0.01 M Tris (pH 7.7) all in 7 M urea. [HArg$^{12}$]glucagon and [dHis$^1$][HArg$^{12}$]glucagon were purified and analyzed on a SP-Sephadex C-25 column (2.5×18 cm) equilibrated in 10% acetic acid containing 20 mM sodium acetate and 1 M urea. The column was developed with 100 ml of buffer, followed by a linear gradient from 0.0 to 0.3 M NaCl (400 ml) and finally 400 ml of 0.5 M NaCl in buffer which eluted [HArg$^{12}$]glucagon from the column.

EXAMPLE 2

Preparation of [dHis$^1$][N$^\alpha$-TNB, HArg$^{12}$]Glucagon

HArg$^{12}$]glucagon was prepared and purified according to the method in Example 1 and 20 mg was dissolved in 2 ml pyridine/H$_2$O/triethylamine (70:30:0.1). The solution was adjusted to pH 10.2 with triethylamine. The sample was deaerated and 100 μl of phenylisothiocyanate was added under nitrogen. The mixture was incubated at 37° C. for 2 h and then extracted three times with benzene (5 ml). The aqueous layer was taken to dryness in vacuo. Trifluoroacetic (10 ml) containing dithiothreitol (3 mg/ml) was added and the sample sealed under nitrogen for 10 min at 50° C. The sample was again taken to dryness in vacuo. [dHis$^1$][HArg$^{12}$]-glucagon was desalted on a Sephadex G-10 column. Further purification was as discussed in Example 1 above.

A trinitrophenyl group was introduced at the N$^\alpha$ position of the serine-2 amino residue by the method described in Example 1. Incorporation of the TNB group was verified through molar extinction coefficients, amino peptidase digestion and acid hydrolysis as described in Example 1.

The following Example illustrates the in vitro stimulatory effects of glucagon, [N$^\alpha$-carbamoyl, N$^\epsilon$-TNB]glucagon, and the preferred analogs of Examples 1 and 2 on liver adenylate cyclase activity.

EXAMPLE 3

Liver plasma membranes were prepared as described by Pohl, et al., *J. Biol. Chem.*, 246, pp. 1849–1856 (1971). The conditions for determining liver adenylate cyclase activity were as described in Bregman, et al., supra, and purification of cyclic AMP was done according to Salomon, et al., *Anal. Biochem.*, 58, pp. 541–548 (1976). Membrane protein was determined utilizing the procedure of Markwell, et al., *Anal. Biochem.*, 87, pp. 206–210 (1978).

As illustrated by the dose-response curves of FIG. 1, endogenous glucagon ( —O— ) produced 100% adenylate cyclase activation at a relatively low concentration. The mixture of glucagon and one μM of the [dHis$^1$][N$^\alpha$-TNB, HArg$^{12}$]glucagon analog (—△—) failed to produce 100% activation with glucagon concentrations three to four times greater than the 100% activation concentration of endogenous glucagon alone. The [N$^\alpha$-TNB, HArg$^{12}$]glucagon analog (1 μM)-glucagon mixture (—□—) showed an even greater competitive inhibitory effect for the analog on adenylate cyclase activity relative to endogenous glucagon, permitting only about one-half the maximal adenylate cyclase activity with glucagon concentrations over 100 times greater than the 100%-activation concentration of the native glucagon alone. The [N$^\alpha$-carbamoyl][N$^\epsilon$-TNB]glucagon (1 μM)-glucagon mixture (—●—), exhibited weaker inhibitory activity for the analog, allowing near 100% activation of the system with glucagon concentrations three to four times that of the native glucagon alone which produced 100% activation.

The following Example illustrates the relative in vitro inhibitory power of [N$^\alpha$-carbamoyl, N$^\epsilon$-TNB]glucagon, [dHis$^1$][N$^\epsilon$-Ptc]glucagon, and the preferred glucagon analogs of Examples 1 and 2.

EXAMPLE 4

Using the data illustrated in FIG. 1 and the lack of stimulatory effect reported in Bregman, et al., supra, for [dHis$^1$, N$^\epsilon$-Ptc]glucagon (Ptc=phenylthiocarbamoyl) on adenylate cyclase activity, the inhibitory strength of the analogs relative to glucagon was determined by comparing the concentration at which the glucagon in the glucagon-glucagon analog mixture produced 50% of the maximum adenylate cyclase activity to the concentration of glucagon alone which produced the 50% activation, and calculated according to the following formula: Relative Inhibitory Strength=(increase K$_a$)/(concentration antagonist)=(K$_a$ (observed)−K$_a$ (glucagon alone)) /1×10$^{-6}$ M, where K$_a$ is the glucagon concentration which induces 50% adenylate cyclase activity. The relative inhibitory strengths of the four analogs are set forth in TABLE I.

TABLE I

| Antagonist | Relative Inhibitory Strength |
|---|---|
| [dHis$^1$][N$^\epsilon$-PTC]-glucagon | 0.055 |
| [N$^\alpha$-carbamoyl, N$^\epsilon$-TNB]-glucagon | 0.010 |
| [dHis$^1$][N$^\alpha$-TNB, HArg$^{12}$]-glucagon | 0.096 |
| [N$^\alpha$-TNB, HArg$^{12}$]-glucagon | 0.540 |

Figure 2:
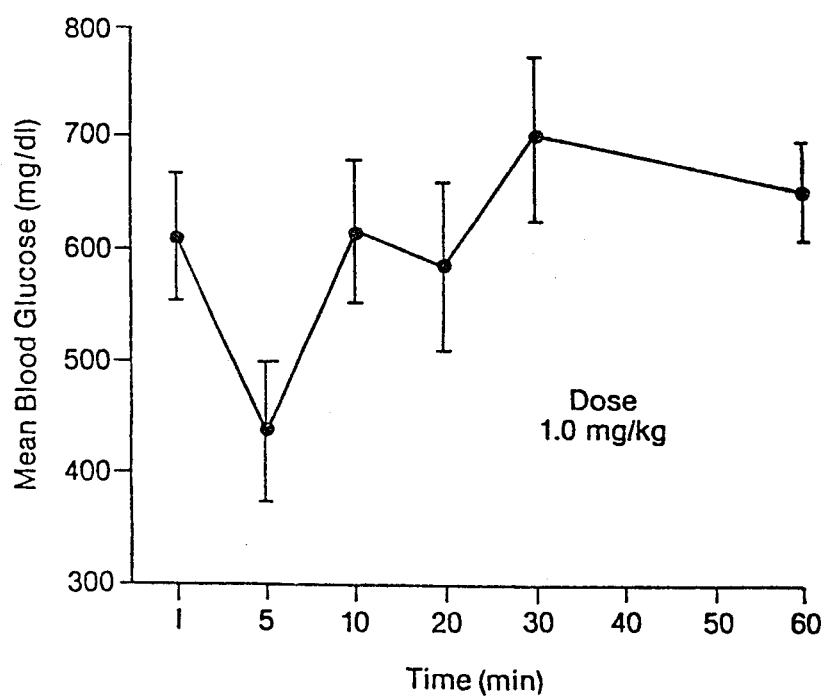

As indicated in TABLE I, [N$^\alpha$-TNB, HArg$^{12}$]glucagon was the strongest relative inhibitor examined, exhibiting a relative inhibitory strength of 0.540, which indicates that the [N$^\alpha$-TNB, HArg$^{12}$]glucagon analog inhibits the adenylate cyclase stimulatory effect of endogenous glucagon at concentrations less than twice as great as the concentration of the native hormone, measured at the 50% activation level. In other words, a concentration of 10$^{-6}$ M of [N$^\alpha$-TNB, HArg$^{12}$]glucagon will inhibit about 0.554×10$^{-6}$ M of glucagon to only 50% activation of the adenylate cyclase system, where only 0.004×10$^{-6}$ M of native glucagon alone will produce the same 50% activation. Also indicated in FIG. 2 are the findings that the other glucagon analogs are weak relative inhibitors of glucose-stimulated adenylate cyclase activity.

The following Example illustrates the preferred method of diminishing the effects of endogenous glucagon in vivo.

EXAMPLE 5

Synthesis and purification of [N$^\alpha$-TNB, HArg$^{12}$]-glucagon was carried out by the methods reported in Example 1 except that the scale of the synthesis was expanded 5–10 fold. This scale-up caused no significant changes in purity as assessed by the methods illustrated in Example 1.

Streptozotocin was obtained from Upjohn Co. Male Wistar rats weighing 310–360 g were made diabetic by intravenous infusion of the streptozotocin, 50 mg/kg, through a tail vein. Immediately prior to infusion the streptozotocin was dissolved in sodium citrate buffer, pH 4.5. The animals were placed in individual metabolic cages to permit measurement of daily urinary glucose excretion. After the amount of glycosuria had stabilized (1–5 weeks), individual rats were anesthetized with intraperitoneal pentobarbital, 65 mg/kg. A jugular vein was catheterized for repetitive blood sampling and infusion of [$N^\alpha$-TNB, HArg$^{12}$]glucagon.

As illustrated in FIG. 2, infusion of a bolus (analog mixed with saline solution) of [$N^\alpha$-TNB, HArg$^{12}$]glucagon, 1.0 mg/kg, produced a rapid decrease in mean blood glucose levels. In this particular experiment, five minutes after administration of the analog, the mean blood glucose fell 28% below baseline levels. Glucose levels returned to normal in about 10–20 minutes and remained stable up to one hour.

Figure 3:
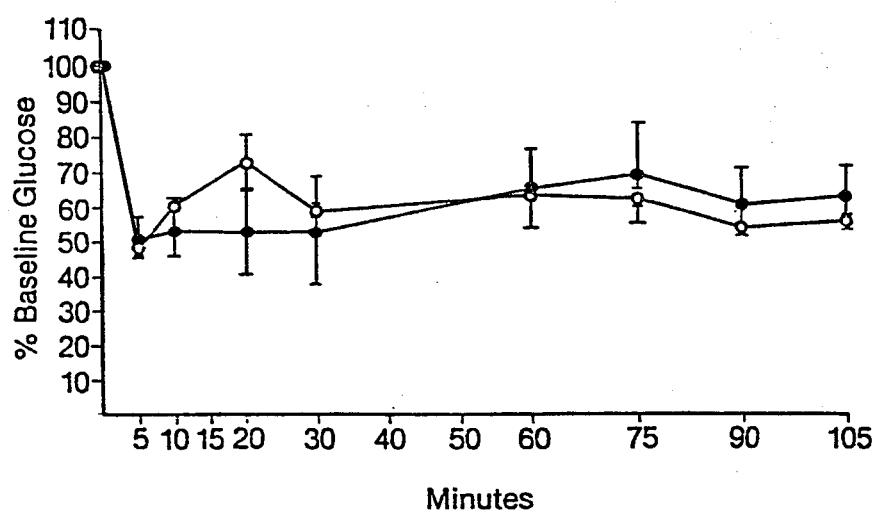

In a second group of experiments anesthetized rats were given a [$N^\alpha$-TNB, HArg$^{12}$]glucagon bolus of 1.0 mg/kg followed immediately by a continuous infusion of the analog, 33 μg/kg·min for 60 min. Glucose from tail blood samples decreased to 67% of baseline at 5 min and remained 30–55% below baseline levels for greater than 90 minutes. Illustrated in FIG. 3 are the observations that comparable decreases in blood glucose were achieved with one-half (0.5 mg/kg bolus, 17 μg/kg·min for 60 min) (— —) and one-tenth (0.1 mg/kg bolus, 3.4 μg/kg·min) (—O—) of this dose. Lower concentrations (1/25 and 1/100 the highest dose) had no discernible effect.

The rapid and substantial lowering of blood glucose levels in diabetic rats by the glucagon antagonist, [$N^\alpha$-TNB, HArg$^{12}$]glucagon, supports the concept that glucagon is an important contributing factor in the hyperglycemia of uncontrolled diabetes. Although some previous studies have suggested that the effect of endogenous glucagon on blood glucose is short-lived [See, Bomboy, et al., Diabetes, 26, p. 177 (1977)], other studies have demonstrated a prolonged increase in hyperglycemia. See, Raskin, et al., Diabetes, 26, p. 1034 (1977). The results with [$N^\alpha$-TNB, HArg$^{12}$]glucagon indicate that in vivo inhibition of the activity of endogenous glucagon receptors with a glucagon antagonist can produce a sustained decrease in blood glucose concentration for at least 105 minutes. The rebound of blood glucose within 10–20 minutes after a single bolus of [$N^\alpha$-TNB, HArg$^{12}$]glucagon was probably due to removal of the antagonist from hepatic receptors rather than any decrease in intracellular hepatic response.

While the method according to Example 5 utilizing the glucagon analog of Example 1 is clearly the presently most preferred and thoroughly tested in vivo procedure of the invention, it is expected that equally effective results may be obtained through use of other semi-synthetic glucagon analogs.

As noted above, compounds useful in the practice of the methods of the invention include those glucagon analogs having a positive charge neutralizing, lipophilic and/or steric-hindering substituent on the $N^\epsilon$ amino group of the lysine-12 amino acid residue and either (1) a positive charge neutralizing, lipophilic and/or steric-hindering substituent on the $N^\alpha$ amino group of histidine, or (2) the $N^\alpha$ histidine amino group deleted and the addition of a positive charge neutralizing, lipophilic, and/or steric-hindering substituent in place thereof, or (3) the $N^\alpha$ histidine amino acid residue deleted with the addition of a positive charge neutralizing, lipophilic and/or steric-hindering substituent to the $N^\alpha$ amino group of serine-2.

The compounds of Examples 1 and 2 illustrate modification of the basic glucagon structure by incorporation of a steric-hindering, guanyl substituent at the $N^\epsilon$ amino group of the native hormone. This particular substituent effects no appreciable positive charge neutralization, nor it is significantly lipophilic. The incorporation of a trinitrobenzene substituent on the $N^\alpha$ amino group of the native hormone or the des-histidine analog thereof functions to neutralize the positive charge on the amino group as well as lend lipophilic and steric-hindering effects.

Other positive charge neutralizing, lipophilic and/or steric-hindering groups which may be incorporated into effective glucagon antagonists include mono- and di-nitro benzene groups.

Numerous suitable carboxylic acid group-containing substituents may be incorporated by formation of amide bonds with amino groups. These include: alkyl carboxylate; amino substituted alkyl carboxylate; phenyl alkyl carboxylate; substituted phenyl alkyl carboxylate, including mono-, di- and tri-alkyl, halo, nitro and hydroxy substituted phenyl alkyl carboxylates; imidazolinyl alkyl carboxylate; naphthyl alkyl carboxylate; benzoate; substituted benzoate including mono-, di- and tri-alkyl, halo, nitro and hydroxy substituted benzoate and alkyl phenyl alkyl benzoate alkenyl carboxylate; phenyl alkenyl carboxylate; substituted phenyl alkenyl carboxylate, including mono-, di- and tri-alkyl, halo, nitro and hydroxy substituted phenyl alkenyl carboxylate; and imidazolinyl alkenyl carboxylate (wherein "alkyl" and "alkenyl" designate $C_1$ to $C_{20}$ straight or branched chain groups).

As examples of phenyl alkyl carboxylate substituents there may be named 3-phenylpropionate and phenylacetate; as substituted phenyl alkyl carboxylate substituents, p-hydroxyphenyl propionate; as imidazolinyl substituted alkyl carboxylate substituents, 3-imidazolpropionate; as naphthyl alkyl carboxylate substituents, α- and β-naphthalenacetate; as substituted benzoate substituents, 4-(4'-ethylphenylmethyl) benzoate; as substituted phenyl alkenyl carboxylate substituents, 3-hydroxyphenyl propenoic acid; as imidazolinyl alkenyl carboxylate substituents, uroconate.

Other substituents may be incorporated by formation of ureas with amino groups. These include: alkyl isocyanate; phenyl isoyanate; substituted phenyl isocyanate, including mono-, di- and tri-alkyl, halo, nitro and hydroxy phenyl isocyanate; and phenyl alkyl cyanate. Substituents may also be incorporated by formation of thioureas with amino groups. These include alkyl isothiocyanate and phenyl isothiocyanate.

Consistent with the foregoing disclosure, numerous modifications and variations in the practice of the invention are expected to occur to those skilled in the art. Consequently, only such limitations as appear in the appended claims should be placed on the invention as above described.

What is claimed is:

1. A method of diminishing glucose levels resulting from endogenous glucagon in a mammal, said method comprising parenterally administering a antagonistically effective amount of an analog of glucagon having a positive charge neutralizing, lipophilic and/or steric-hindering substituent on the $N^\epsilon$ amino group of the lysine-12 residue and either (1n) a positive charge neutralizing, lipophilic and/or steric-hindering substituent on the $N^\alpha$ amino group of histidine, or (2) the $N^\alpha$ histidine amino group deleted with the addition of a positive charge neutralizing, lipophilic and/or steric-hindering substituent in place thereof, or (3) the $N^\alpha$ histidine amino acid residue deleted with the addition of a positive charge neutralizing, lipophilic and/or steric-hindering substituent to the amino group of serine-2.

2. The method of claim 1 wherein the substituent on the $N^\epsilon$ amino group of the lysine-12 residue is a guanyl substituent.

3. The method of claim 1 wherein the substituent on the $N^\epsilon$ amino group of the lysine-12 residue is a trinitrophenyl substituent.

4. The method according to claim 1 wherein a trinitrophenyl substituent is on the $N^\alpha$ amino group of histidine.

5. The method according to claim 1 wherein the $N^\alpha$ histidine amino acid residue is deleted and a trinitrophenyl substituent is on the amino group of serine-2.

6. The method according to claim 1 wherein the glucagon analog is [1-$N^\alpha$-trinitrobenzene, 12-homoarginine]glucagon.

7. The method according to claim 1 wherein the glucagon analog is [1-des-histidine] [2-$N^\alpha$-trinitrobenzene, 12-homoarginine] glucagon.

8. The method according to claim 1 wherein the quantity of glucagon analog parenterally administered is from about 0.05 to about 50 mg per kg of body weight of the mammal.

9. The method according to claim 8 wherein the quantity of glucagon analog parenterally administered is from about 0.1 to about 10 mg per kg of body weight of the mammal.

10. The method according to claim 1 wherein the positive charge neutralizing, lipophilic and/or steric-hindering substituent is selected from the group consisting of: mono- and di-nitro benzene; alkyl carboxylate; amino substituted alkyl carboxylate; phenyl alkyl carboxylate; substituted phenyl alkyl carboxylate, including mono-, di-and tri-alkyl, halo, nitro and hydroxy substituted phenyl alkyl carboxylate; imidazolinyl alkyl carboxylate; naphthyl alkyl carboxylate; benzoate; substituted benzoate, including mono-, di- and tri-alkyl, halo, nitro and hydroxy substituted benzoate and alkyl phenyl alkyl benzoate; alkenyl carboxylate; phenyl alkenyl carboxylate; substituted phenyl alkenyl carboxylate, including mono-, di- and tri-alkyl, halo, nitro and hydroxy substituted phenyl alkenyl carboxylate; imidazolinyl alkenyl carboxylate; alkyl isocyanate; phenyl isocyanate; substituted phenyl isocyanate, including mono-, di- and tri-alkyl, halo, nitro and hydroxy phenyl isocyanate; phenyl alkyl isocyanate; alkyl isothiocyanate; and phenyl isothiocyanate.

11. A pharmaceutical composition for use in diminishing glucose levels resulting from endogenous glucagon in mammals, said composition comprising an effective amount of:

an analog of glucagon having a positive charge neutralizing, lipophilic and/or steric-hindering substituent on the $N^\epsilon$ amino group of the lysine-12 residue and either (1) a positive charge neutralizing, lipophilic and/or steric-hindering substituent on the $N^\alpha$ amino group of histidine, or (2) the $N^\alpha$ histidine amino group deleted with the addition of a positive charge neutralizing, lipophilic and/or steric-hindering substituent in place thereof, or (3) the $N^\alpha$ histidine amino acid residue deleted with the addition of a positive charge neutralizing, lipophilic and/or steric hindering substituent to the amino group of serine-2; and a pharmaceutically acceptable diluent, adjuvant or carrier.

12. A method of diminishing glucose levels resulting from endogenous glucagon in a mammal, said method comprising parenterally administering an antagonistically effective amount of an analog of glucagon selected from the group comprising [1-$N^\alpha$-trinitrobenzene, 12-homoarginine]glucagon, and [1-des-histidine][2-$N^\alpha$-trinitrobenzene, 12-homoarginine]glucagon.

13. The method according to claim 12 wherein the quantity of glucagon analog parenterally administered is from about 0.05 to about 50 mg per kg of body weight of the mammal.

14. The method according to claim 13 wherein the quantity of glucagon analog parenterally administered is from about 0.1 to about 10 per kg of body weight of the mammal.

15. A pharmaceutical composition for use in diminishing glucose levels resulting from endogenous glucagon in mammals, said composition comprising an effective amount of:

an analog of glucagon selected from the group comprising [1-$N^\alpha$-trinitrobenzene, 12-homoarginine]-glucagon, and [1-des-histidine][2-$N^\alpha$-trinitrobenzene, 12-homoarginine]glucagon and a pharmaceutically acceptable diluent, adjuvant or carrier.

* * * * *

UNITED STATES PATENT AND TRADEMARK OFFICE
CERTIFICATE OF CORRECTION

PATENT NO. : 4,430,326

DATED : February 7, 1984

INVENTOR(S) : Hruby, et al.

It is certified that error appears in the above-identified patent and that said Letters Patent is hereby corrected as shown below:

Column 1, line 27, "Ser Gln" should read --Ser=serine; Gln--.

Column 1, line 38, "$\delta$" should read --$\gamma$--.

Column 1, line 59, "See, White" should read --(See, White--

Column 2, line 4, "diabetes See," should read --diabetes. See,--.

Column 2, line 6, "'bihormonal$^\epsilon$'" should read --'bihormonal'--.

Column 3, line 6, "$N^{60}$" should read --$N^\alpha$--.

Column 3, line 15, "(=[$N^\epsilon$" should read --(=[$N^\alpha$--.

Column 3, line 58, after "substituent" add --in place thereof--.

Column 4, line 50, "BaS0$_4$" should read --BaSO$_4$--.

Column 4, line 53, "4°C." should read --4°C--.

UNITED STATES PATENT AND TRADEMARK OFFICE
CERTIFICATE OF CORRECTION

PATENT NO. : 4,430,326

DATED : February 7, 1984

INVENTOR(S) : Hruby, et al.

It is certified that error appears in the above-identified patent and that said Letters Patent is hereby corrected as shown below:

Column 5, line 8, "5°C." should read --5°C--.

Column 5, line 22, "HArg$^{12}$]" should read --[HArg$^{12}$]--.

Column 5, line 28 "37°C." should read --37°C--.

Column 5, line 59, "(----0----)" should read --(----0----)--.

Column 7, line 32, "(---- ----)" should read --(----●----)--.

Column 7, line 64, "N$^\epsilon$amino" should read --N$^\epsilon$ amino--.

Column 8, line 32, "benzoate alkenyl" should read --benzoate; alkenyl--.

Column 8, line 52, "phenyl isoyanate" should read --phenyl isocyanate--.

Column 8, line 67, "a antagonistically" should read --an antagonistically--.

UNITED STATES PATENT AND TRADEMARK OFFICE
CERTIFICATE OF CORRECTION

PATENT NO. : 4,430,326

DATED : February 7, 1984

INVENTOR(S) : Hruby, et al.

Page 3 of 3

It is certified that error appears in the above-identified patent and that said Letters Patent is hereby corrected as shown below:

Column 9, line 3, "(ln)" should read --(1)--.

Column 10, line 16, "or (2)" should read --(2)--.

Column 10, line 22, "steric hindering" should read --steric-hindering--.

Column 10, line 39, "10 per kg" should read --10 mg per kg--.

Signed and Sealed this

Twelfth Day of March 1985

[SEAL]

Attest:

DONALD J. QUIGG

Attesting Officer

Acting Commissioner of Patents and Trademarks